(12) United States Patent
Rey

(10) Patent No.: US 8,096,190 B2
(45) Date of Patent: Jan. 17, 2012

(54) PROCESS FOR CONDUCTING ADHERENCE TESTS FOR A COATING ON A SUBSTRATE

(75) Inventor: Stephane Rey, Lacasse (FR)

(73) Assignee: Airbus France, Toulouse (FR)

( * ) Notice: Subject to any disclaimer, the term of this patent is extended or adjusted under 35 U.S.C. 154(b) by 740 days.

(21) Appl. No.: 11/673,003

(22) Filed: Feb. 9, 2007

(65) Prior Publication Data

US 2007/0228591 A1 Oct. 4, 2007

(30) Foreign Application Priority Data

Feb. 15, 2006 (FR) ...................................... 06 50543

(51) Int. Cl.
*G01N 19/04* (2006.01)
(52) U.S. Cl. .......... 73/827; 73/150 A; 73/842; 264/40.1; 264/260; 425/121; 425/127
(58) Field of Classification Search .................. 264/259, 264/40.1, 260; 73/150 A, 827, 842; 425/121, 425/127
See application file for complete search history.

(56) References Cited

U.S. PATENT DOCUMENTS

| 3,821,892 | A | * | 7/1974 | Saberg ............................ 73/827 |
| 4,263,811 | A | * | 4/1981 | Shaw .............................. 374/50 |
| 4,346,602 | A | | 8/1982 | Gould et al. |
| 4,501,154 | A | * | 2/1985 | Mori ............................... 73/827 |
| 5,337,614 | A | * | 8/1994 | Jiang et al. ...................... 73/827 |
| 5,639,416 | A | * | 6/1997 | Pennisi et al. ................. 264/571 |
| 6,176,141 | B1 | * | 1/2001 | Chuang et al. .............. 73/150 A |
| 6,289,741 | B1 | * | 9/2001 | Ghetzler et al. ................ 73/827 |
| 6,324,916 | B1 | | 12/2001 | Jessop |
| 6,450,798 | B1 | * | 9/2002 | Choi et al. .................... 425/572 |
| 6,523,419 | B1 | * | 2/2003 | Nonaka et al. .................. 73/827 |
| 7,226,559 | B2 | * | 6/2007 | Maxwell et al. .............. 264/511 |

* cited by examiner

*Primary Examiner* — Joseph Del Sole
*Assistant Examiner* — Timothy Kennedy
(74) *Attorney, Agent, or Firm* — Perman & Green, LLP

(57) ABSTRACT

In order to conduct tests designed to determine the adherence properties of a coating on a substrate, a pull plate of a hard-enable material is molded directly to the surface of a coating applied to a substrate. The pull plate geometry is determined by the mold cavity and is made of a material that adheres to the coating surface during the molding process. The pull plate therefore, is only used once, while the mold may be reused.

23 Claims, 5 Drawing Sheets

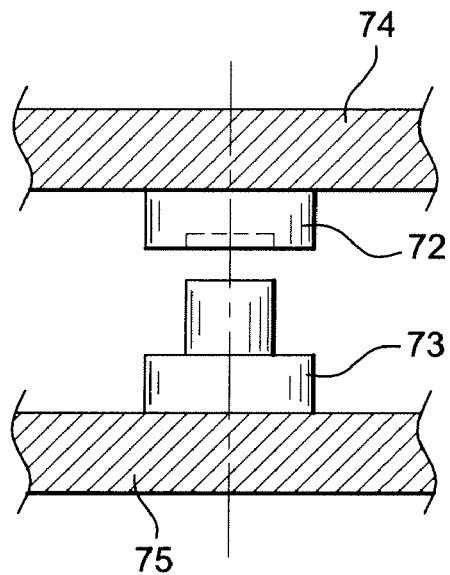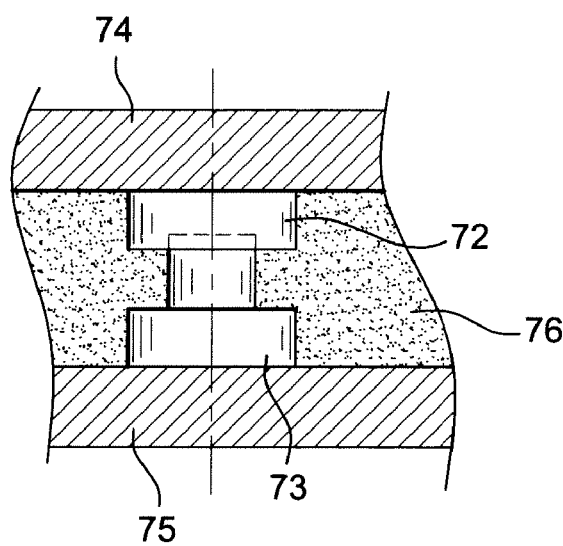
Fig. 14a  Fig. 14b
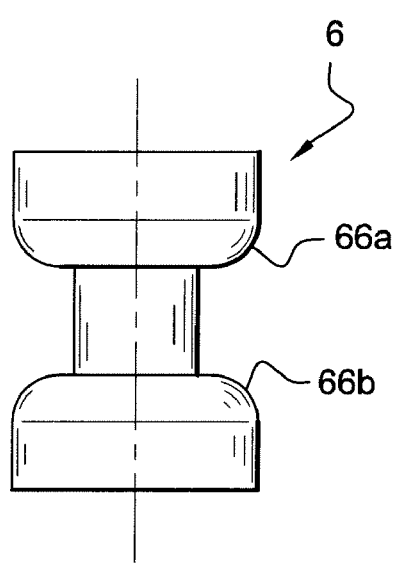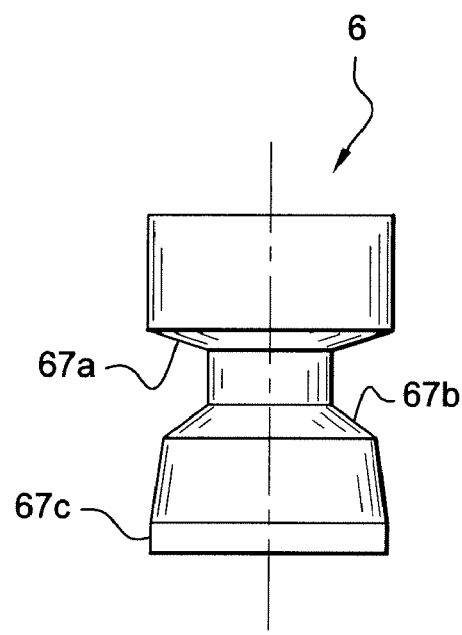
Fig. 15a  Fig. 15b

PROCESS FOR CONDUCTING ADHERENCE TESTS FOR A COATING ON A SUBSTRATE

FIELD OF THE INVENTION

The present invention relates to devices used to measure the adhesion properties of coatings such as paints, surface protections, glues or adhesive films on the substrates for which they are designed, or to measure the cohesion properties of surfaces in general. More particularly, the invention concerns a process for preparation of adherence tests using pull plates that are fastened to the surface whose adhesion performance must be measured by exerting a tearing force by means of said pull plates.

PRIOR ART

Knowledge of the adhesion properties of a coating on a substrate, for example a paint, a varnish or an adhesive on its intended support, or the cohesion of the surface of a material is an essential piece of information, since these properties greatly affect the behavior of these parts and assemblies of these parts in their future functional environments, as well as the behavior over time of surface protections and decorations.

One method currently used to determine such adhesion properties of a coating or the cohesion properties of a surface consists of measuring the forces necessary on a test piece to induce tearing away of a coating sample from a substrate on which a material has been deposited or the tearing away of parts of the surface of a material.

Most often the tests are conducted on standardized test pieces and follow well-defined protocols, since it is useful to be able to reproduce the measurements in a repetitive manner to effectively compare the adhesion performances of different coating-substrate pairs.

The general principle of such a measurement consists of gluing a rigid plate of calibrated gluing surface onto a surface sample to be evaluated, i.e., a substrate coated with a coating according to the application process provided or a sample of material having undergone surface treatments, and, after the glue sets, pulling on the plate until the coating tears away from the substrate surface or its surface material is torn away.

The force corresponding to this tearing away gives a measurement of the adhesion or cohesion properties investigated.

ISO standard 4624 describes a procedure to be implemented so that the results obtained by different test laboratories can be compared.

Pulling devices are also found, such as the one described in U.S. Pat. No. 3,821,892, which are implemented to conduct the tests in question. The device described permits exerting a pulling force on a glued plate in the form of a "dolly" and is equipped with means for measuring the pulling force applied.

Experience shows that the quality of the results obtained during implementation of ISO Standard 4624 is strongly linked to the quality of gluing the plate and to the preparation quality of the test. Most of the time these preparation and gluing qualities are not completely satisfactory, which greatly disrupts the measurements of tearing forces.

In fact, due to the fluidity of the glue when the plate is glued onto the surface of the test piece, it is very difficult to control the homogeneity of the thickness of the glue film between the pull plate and the test piece and to guarantee that the axis of the plate is perfectly perpendicular to the surface of the test piece. In practice, a deviation, even a small one, from the axis of the plate with regard to the pulling axis and a variation of the film thickness of the glue at the interface between the pull plate and the coating tested perceptibly affect the value of the force measured at the time of tearing away, an effect which is even more disadvantageous, since due to its random nature, it leads to a significant scatter of measurements.

In order to take this phenomenon into account, the test operator is generally led to repeat the tests a large number of times in order to provide usable mean values of the tearing forces.

The positioning of such pull plates on the test pieces has therefore proven costly due to the preparation time and due to the multiplication of necessary tests, as well as by the cost of the pull plates themselves.

These pull plates are most often made of metal, which permits cleaning them after each test by mechanically eliminating glue residues, but, on the one hand, this cleaning is itself costly, and, on the other hand, the accumulation of damage to the pull plate by tests and successive cleanings limits the effective number of re-uses of each plate.

DISCLOSURE OF THE INVENTION

The present invention proposes resolving these difficulties by means of a preparation process for pulling tests that eliminates the operations of gluing the pull plates as such and that uses single-use pull plates created at the very surface of the sample to be tested.

Thus, in order to implement the preparation process for a test of adherence of a coating on a substrate by means of at least one pull plate, the at least one pull plate is made of a material that can be hardened on the coating before being subjected to the adherence test.

Said at least one pull plate made of a hardenable material is shaped in a mold, said mold comprising a lower surface positioned on the coating to be tested, said mold comprising at least one hollow cavity having the shape of a pull plate, and said at least one hollow cavity comprising an opening on the lower surface of the mold in contact with the coating to be tested.

The space between the lower surface of the mold and the coating to be tested is tightly sealed, outside the opening on said lower surface, for example, by means of shaping said lower surface of the mold coordinated to the shape of the substrate on which the coating to be tested is deposited.

In one alternative solution, the tight seal sought is obtained by the choice of a material for creating the mold that can mate with the shape of the substrate on which the coating to be tested is deposited.

In another alternative solution, the tight seal sought is obtained by means of a padding or bead of the mold material forming an excrescence along the perimeter of the opening of the at least one hollow cavity on the lower surface of the mold, or by means of a removable joint in a groove along said perimeter.

When the process is implemented, the at least one hollow cavity is filled with the hardenable material through an opening of said at least one cavity which opens up onto a mold surface other than the lower surface.

In one particular embodiment, said opening roughly corresponds to the upper surface of the pull plate corresponding to the at least one hollow cavity, or corresponds to one end of a pouring shaft leading into the at least one hollow cavity.

In another embodiment, said opening corresponds to one end of an injection channel leading into the at least one hollow cavity.

Advantageously, the air contained in the at least one hollow cavity is evacuated during the filling of said cavity with the hardenable material by means of a shaft emerging on a surface of the mold other than the lower one.

Advantageously, the process implements a mold comprising two or more pull-plate hollow cavities.

The hollow cavities are preferably connected by channels that can permit the passage of hardenable material between the hollow cavities during the pouring operation.

After hardening of the hardenable material, the mold is removed to release the at least one pull plate by acting on the capacity of the mold to be deformed.

The mold can also be made of at least two elements that can be separated to more easily release the at least one pull plate.

In another embodiment of the process, the mold is destroyed in order to release the at least one pull plate after the hardening of the hardenable material.

The mold can be made by using a silicone resin, and the shape of the at least one pull plate hollow cavity is advantageously adapted to the implementation of the process, for example, by creation of coupling neck-molding pieces or inclined surfaces that facilitate removal of the mold after hardening of the hardenable material.

The hardenable material used in the process can be a polymerizable material such as an epoxy or acrylic or polyurethane resin. This material can also be a fusible material.

In a particular form of implementation of the process, a core of greater strength than the hardenable material is inserted roughly along the axis of at least one hollow cavity before or during the operation of pouring the hardenable material. A shoulder on the core permits reinforcing the zone of the plate used in creating the pull.

DESCRIPTION OF THE DRAWINGS

The detailed description of the process according to the invention is made in reference to FIGS. 1 to 15 which show:

FIG. 14: illustration of a process for creating a mold by filling the space comprised between two discs. In FIG. 14a the discs are separated, and in FIG. 14b the discs are in position for filling.

FIG. 15: modified forms of pull plates to facilitate the implementation of the process.

DETAILED DESCRIPTION OF THE INVENTION

Figure 1:
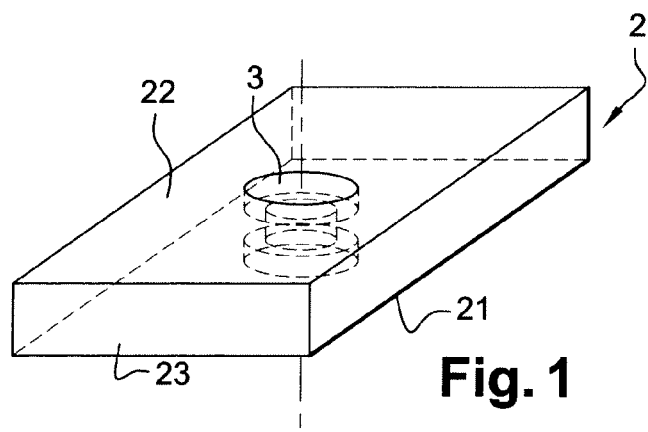
FIG. 1: a mold for a pull plate before being applied onto the surface to be tested during the first step of the process.

According to the process, a first step comprises the positioning, on the surface of a test piece 1, of a mold 2 that has at least one cavity 3 corresponding to a hollow form for a pull plate. Test piece 1 is made up of a substrate 11, generally flat, coated with a coating 12 such as a paint, a varnish or an adhesive film. The assembly of substrate 11 and coating 12 constitutes a pair, combined in a preparation process, that one wishes to subject to the adherence test.

Mold 2 has a lower surface 21 that, due to the shape of mold 2 and due to the means used (not shown) for holding it in place at the surface of test piece 1, is such that said lower surface 21 that is placed in contact with the surface to be tested more or less takes on the shape of the surface of test piece 1.

In a second step, a hardenable material 5 (that is to say, a material that can be hardened from a fluid state, for example by polymerization or by cooling) and adhesive is poured into cavity 3 for at least one pull plate.

In a third step, after hardening of hardenable material 5, mold 2 for the pull plates is removed to leave at least one pull plate of hardened hardenable material adhering to the surface of test piece 1.

Test piece 1 thus provided with at least one pull plate 6 is then ready to be subjected to the test.

Mold 2 used for the implementation of the process comprises at least one hollow 3 for at least one pull plate, i.e., a hollow form having the contours of the outer surface of a pull plate whose dimensions conform to the test protocol that must be implemented. Advantageously, mold 2 comprises two or more hollow forms 3, 3a, 3b, 3c, 3d, 3e, each corresponding to a pull plate, permitting creating two or more pull plates on the same test piece 1 according to the process, in order to be able to conduct a series of tests on the same test piece 1.

Each hollow form 3, 3a, 3b, 3c, 3d, 3e in mold 2 corresponding to the cavity for one pull plate emerges via an opening 31 on lower face 21 of the mold, i.e., the face in contact with test piece 1 when mold 2 is positioned after the first step of the process, so that opening 31 corresponds by its dimensions to the surface of a pull plate 6 that must be created on the surface of the test piece. Axis 32 of this hollow form, and therefore axis 62 of the pull plate that will be made by molding in said hollow form 3, is roughly perpendicular to the plane of opening 31, i.e., to the surface of test piece 1 when mold 2 is in place after the first step of the process.

Cavity 3 for each pull plate has at least one opening emerging directly or indirectly on a face of mold 2 other than lower face 21.

In a first embodiment, the process uses a mold 2 in which pull plate cavities 3, 3a, 3b, 3c, 3d, 3e open onto a face of the mold called upper face 22, i.e., a face situated on the opposite side of mold 2 relative to lower face 21, by at least one opening.

Figure 4:
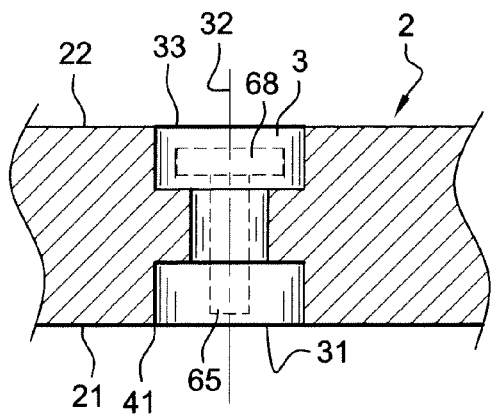
FIG. 4: section of a first mold form that can be used for implementing the process.

In one particular form of mold 2 presented in FIG. 4, called form A, designed for implementing the process according to said first embodiment, each pull-plate cavity 3 opens onto upper surface 22 of mold 2 via an opening 33 that roughly corresponds to upper surface 64 of pull plate 6, i.e., the surface of pull plate 6 at the opposite end of said plate relative to the surface which is glued onto test piece 1.

Figure 5:
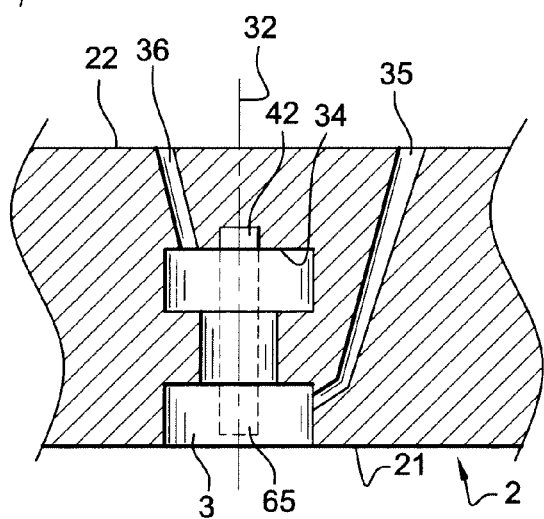
FIG. 5: section of a second mold form that can be used for the implementation of the process. This figure also illustrates the case of a core inserted into the mold to reinforce the pull plate of hardened material.
Figure 6:
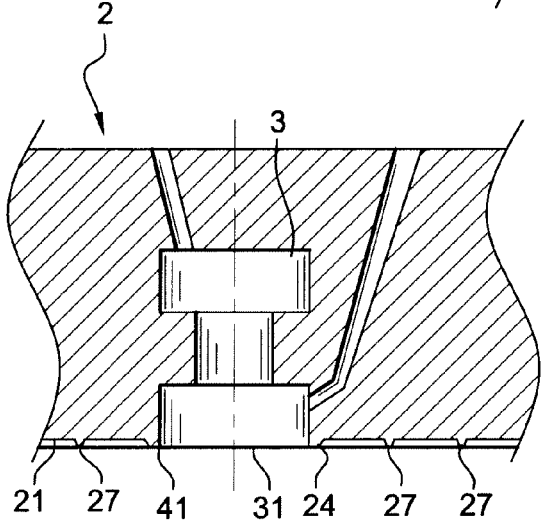
FIG. 6: section of a mold form having a padding or bead made with the material used for creating the mold to assure the tight seal between the mold and the test piece surface.
Figure 7:
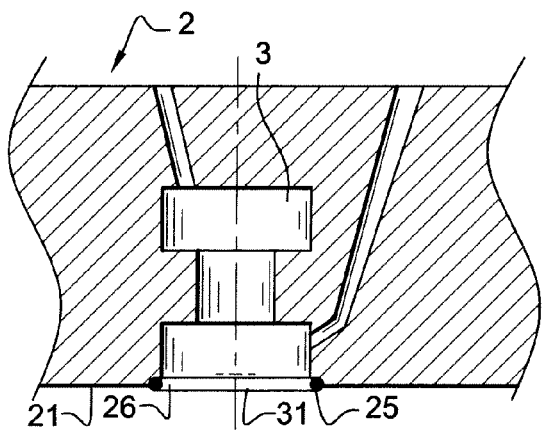
FIG. 7: section of a mold form having a joint inserted into a groove created in the mold to assure the tight seal between the mold and the surface of the test piece.

In another particular form of mold 2 shown in FIG. 5, called form B, also designed for implementing the process according to said first embodiment, pull plate cavity 3 is closed overall at the level of upper surface 34 of the pull plate cavity and is connected to upper face 22 of mold 2 by means of at least one pouring shaft 35. Preferably, at least one second shaft 36 is arranged between upper part 34 of pull-plate cavity 3 and upper face 22 of mold 2 in order to serve as a vent and prevent the formation of air pockets in cavity 3 during the pouring of hardenable material 5.

In a second embodiment, the process uses a mold 2 in which pull-plate cavity or cavities 3a, 3b, 3c, 3d, 3e are open to the outside of mold 2 by at least one injection opening 37 that emerges on a face of mold 2 other than lower face 21, for example, upper face 22, or a lateral face 23. Preferably, at least one second opening 38, 38a, 38b, 38c, 38d, 38e is arranged to serve as a vent between pull-plate cavity or cavities 3a, 3b, 3c, 3d, 3e and a mold face other than lower face 21.

Figure 8:
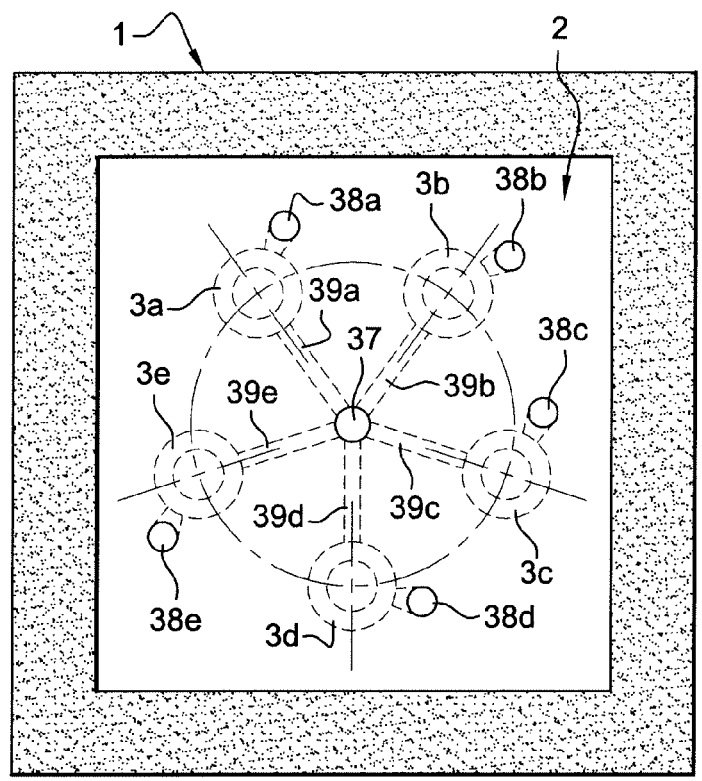
FIG. 8: top view of a mold having an example of the "star" arrangement to create several pull plates with the same mold by injection of hardenable material.

In one particular form of the mold presented in FIG. 8, called form C, designed for implementing the process according to said second embodiment, injection opening 37 is situated on upper face 22 of mold 2 and can distribute to one, two or more pull-plate cavities 3a, 3b, 3c, 3d, 3e, for example arranged in a star shape, and each pull-plate cavity has at least one vent whose opening 38a, 38b, 38c, 38d, 38e is also situated on upper surface 22 of mold 2.

Figure 9:
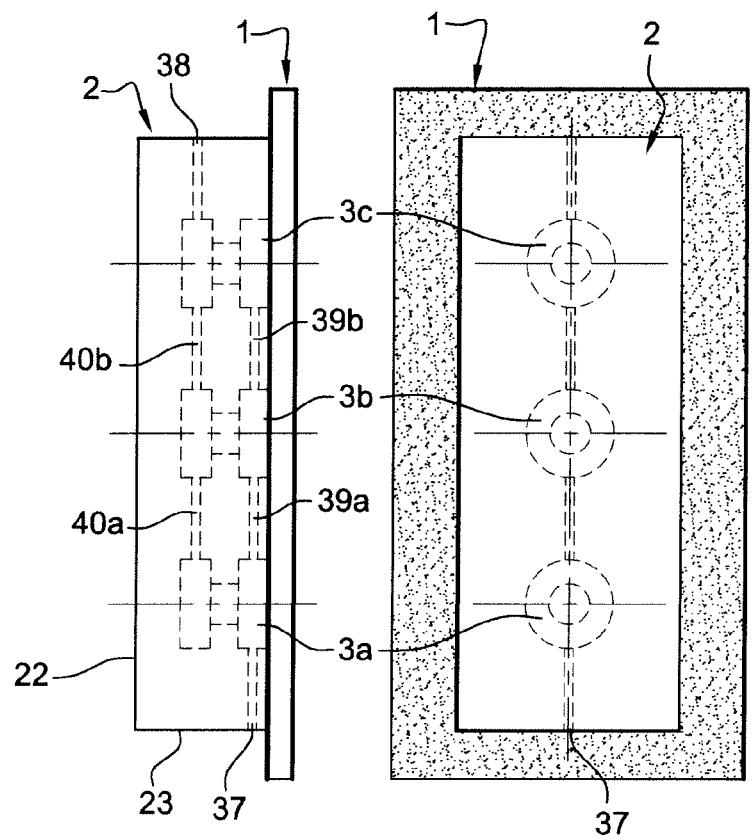
FIG. 9: example of the "line" arrangement to create several pull plates with the same mold by injection of hardenable material.

In a particular form of the mold presented in FIG. 9, called form D, also designed for implementing the process according to the second embodiment, said at least one injection opening 37 and the at least one vent opening 38 are situated on lateral face 23 of mold 2 in places roughly opposite the one or more pull-plate cavity or dies 3a, 3b, 3c so that during the filling of the one or more cavities 3a, 3b, 3c by hardenable material 5 injected through said injection opening 37, said one or more cavities are filled progressively by hardenable material 5 and the air contained in the one or more cavities is evacuated by vent 38 without being opposed.

When two or more pull-plate cavities 3a, 3b, 3c, 3d, 3e are created in the same mold 2, said mold advantageously comprises communication channels 39a, 39b, 39c, 39d, 39e, 40a, and 40b between the different pull-plate cavities, which can assure the flow of hardenable material 5 as well as the evacuation of air during the second step of the process.

During the implementation of the first step of the process, i.e., positioning of mold 2 on test piece 1, it is important that the contact between mold 2 and test piece 1 along perimeter 41 of lower opening 31 of pull-plate cavity 3 on lower face 21 of mold 2 is such that hardenable material 5 remains contained in cavity 3 during the molding operation and does not flow between mold 2 and the surface of test piece 1 beyond this perimeter 41. It is easily understood that leaks at this level would lead to an uncontrollable modification of the contact surface of pull plate 6 with test piece 1, and therefore of the quality of measurements of the tearing away of coating 12.

Such a result is obtained by intimate contact, at least locally, in the zone around lower opening 31 of pull-plate cavity 3 and the surface of test piece 1, a contact that is obtained, for example, by:
  a shape of lower surface 21 of mold 2 coordinated to the shape of the surface of test piece 1 (generally flat) and/or
  means (not shown) for holding mold 2 in place on test piece 1 assuring sufficient pressure, and/or
  a material used for creating mold 2 presenting elasticity and/or triboelectricity characteristics permitting it to mate to the shape of the surface of test piece 1, and/or
  a padding or bead 24, 25 of material at periphery 41 of lower opening 31 of pull-plate cavity 3, which can assure the tight seal between mold 2 and test piece 1, said bead being able to be formed by an excrescence 24 of the material used to create mold 2, or a removable joint 25, for example, an O-ring positioned in a recess 26.

In this latter alternative, in order to form the bead, an excrescence 24 of the material of mold 2 is advantageously created if this material has a sufficient elasticity to act as a joint, and preferably excrescences 29 of roughly the same height are distributed on lower face 21 of the mold to guarantee the stability and perpendicularity of the axis of cavity 3 with the surface of test piece 1. These excrescences 29 can be of varied shapes, such as spikes or straight or curved lines. Advantageously, a removable joint 25 is used if the material is too rigid for an excrescence, in order to offer the necessary deformation properties to assure the desired tight seal. In this case, joint 25 is mounted as flush as possible to guarantee the tight seal sought without risking altering the perpendicularity of axis 32 of cavity 3 relative to the surface of test piece 1 during clamping of mold 2 onto said surface.

Mold 2 can be created of any material whatever that permits obtaining the characteristics thus sought, with the reservation that the material used must not be perceptibly degraded by the hardenable material 5 used for creating pull plates 6, which could, for example, induce a chemical attack of the material of mold 2, and with the reservation that it has dimensional stability, in particular rigidity, in order to guarantee that pull plates 6 that have been created will have the desired dimensions and shape.

Pull plate hollow cavities 3, 3a, 3b, 3c, 3d, 3e in mold 2 can be made by cutting, or by any machining process suited to the material used to create mold 2. Mold 2 itself can also be created by molding.

Figure 10:
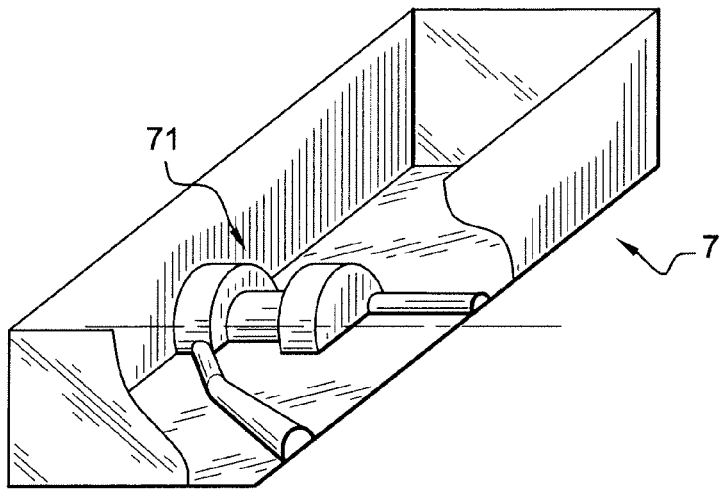
FIG. 10: example of device to create a mold element by molding.

A particularly advantageous process for creating mold 2 illustrated in FIG. 10 consists of pouring a resin, for example a silicone resin, into a container 7 having the general shape of mold 2 or of an element of the mold, and in which are positioned inserts 71, fixed or removable, having the geometry of hollow forms before being arranged in mold 2, including possible pouring shafts, vents, and communication channels.

When the resin is polymerized, the block that it makes up is removed from the container and, possibly after extraction of removable inserts from said block, leaves the shapes of the hollow mold in the polymerized resin.

Resin, in particular silicone resin, thus permits creating less costly molds, which are easy to manipulate due to the good mechanical strength of the resin; the resin also has an excellent resistance to chemical attack and good dimensional properties, while having an elasticity that permits obtaining the sought intimate contact with the surface of the test piece during the first step of the process, i.e., the joining of mold 2 in one or more elements with test piece 1.

In order to realize the second step of the process for creating the pull plate, i.e., to fill hardenable material 5 in the fluid state into one or more cavities 3, 3a, 3b, 3c, 3d, 3e of the mold, the assembly of mold 2 and test piece 1 is held in a position suited to this filling.

Figure 2:
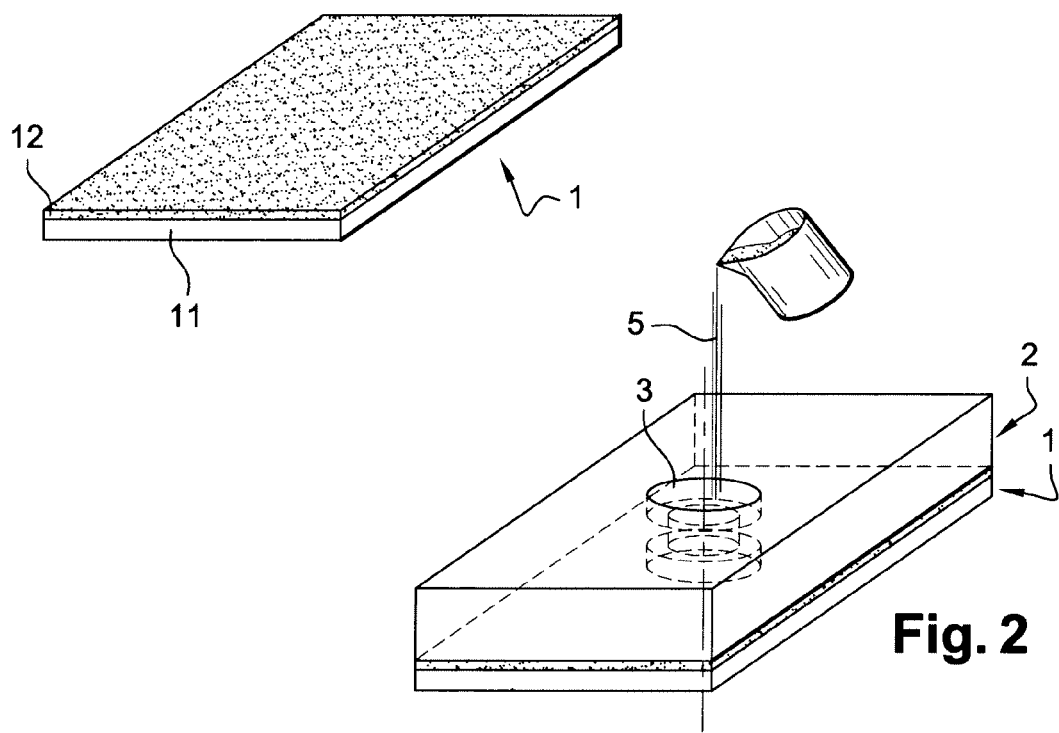
FIG. 2: operation of filling the mold with a hardenable material during the second step of the process.
Figure 3:
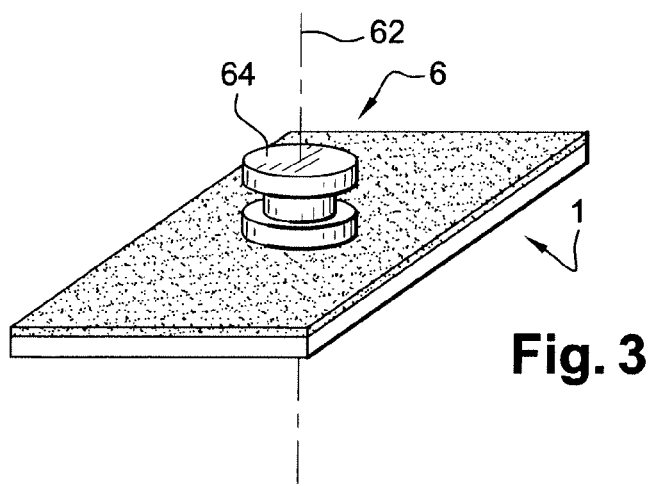
FIG. 3: the pull plate of hardened hardenable material at the surface of a test piece after the mold has been removed.

In the case of a gravity filling such as the example illustrated in FIGS. 4 and 5, or by injection in the direction of gravity such as illustrated in FIG. 8, these openings 33, 35, 37 for introduction of the hardenable material are positioned on the top part. For example, in the configuration of mold 2 corresponding to form A or to form B, the assembly of mold 2 and test piece 1 is placed in a position roughly horizontal with the openings of upper face 22 of mold 2 directed towards the top as illustrated in FIG. 2. Hollow cavities 3, 3a, 3b, 3c, 3d, 3e are then filled with hardenable material 5, for example by gravity, and the assembly of mold 2 and test piece 1 is held in position until the hardening of hardenable material 5 which fills said hollow cavities.

In the case of molds corresponding to form C or form D, the assembly of mold 2 and test piece 1 is positioned so that vent or vents 38, 38a, 38b, 38c, 38d, 38e prevent the formation of air pockets during the filling of the hollow forms. In these cases, filling is advantageously carried out by introducing hardenable material 5 via the lower part of the hollow forms, the air being evacuated during this operation by vents at the top part of the hollow forms.

The third step of the creation process consists of removing mold 2 in order to release the at least one pull plate 6 of hardenable material 5 that is hardened to the surface of test piece 1.

In a first method of implementation of said third step of the process, mold 2 is removed by exerting sufficient pulling forces on the mold so that the at least one pull plate 6 is removed from mold 2.

When mold 2 is made of a single element, due to a shape that generally does not permit being removed from the mold and that is used for the pull plates, it is not possible to remove mold 2 without damaging either the mold or the pull plates, unless mold 2 is made of a material that can be deformed, at least temporarily, due to its elasticity. Such a result is obtained, for example, by making mold 2 of an elastomer such as silicone resin or a rubber.

In this first method for implementing the third step of the process, it is advantageous to use a mold 2 made up of two or more elements 27a, 27b, so that the operation of removing mold 2 or mold elements 27a, 27b avoids, or at least limits, deformations of the mold, and therefore the risks of damaging mold 2, so that said mold can be reused.

Figure 11:
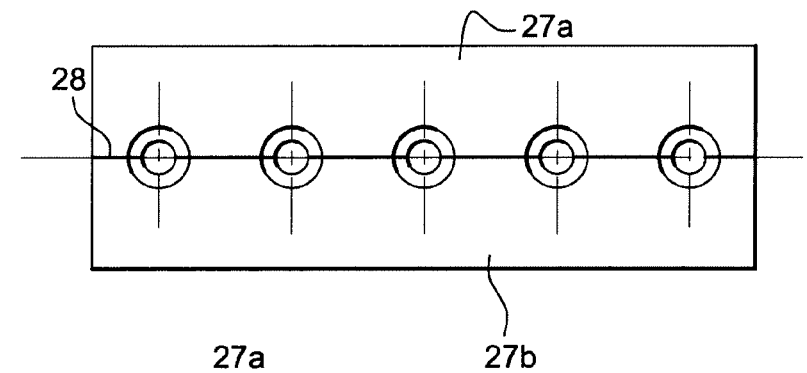
FIGS. 11, 12 and 13: arrangement of hollow cavities for pull plates in molds of two separable elements to facilitate the removal of the pull plates from the mold.

For example, a mold 2 for creating a pull plate or several aligned pull plates is advantageously made of at least two separable elements, for example, as illustrated in FIG. 11, roughly along a plane of symmetry 28 passing through the one or more axes 32 of the pull-plate cavities, so that the at least two elements 27a, 27b can be laterally removed with minimal deformation of mold 2 and minimal parasitical forces on the pull plates.

Figure 12:
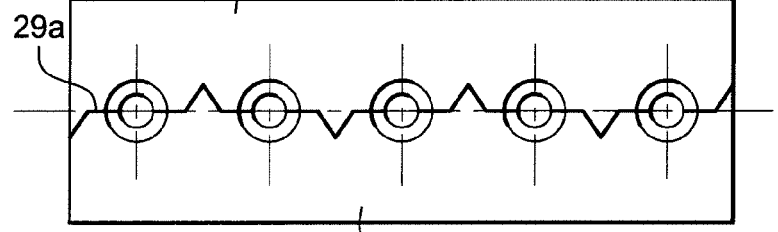
Figure 13:
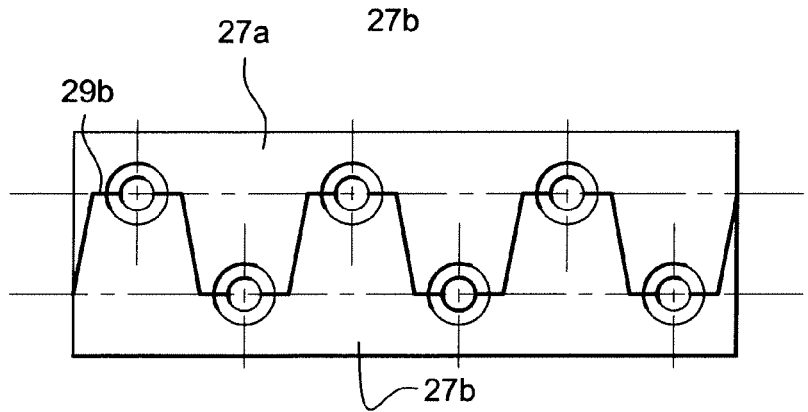

In the particular embodiments illustrated in FIG. 12 and FIG. 13 of a mold 2 made of two or more elements, separation surface 29a, 29b, between the different elements of the mold, has a succession of planes whose arrangement permits both jointing and removing the elements and improves the positioning precision relative to the mold elements by preventing sliding movements between said elements.

This particular embodiment also allows an arrangement of the pull plates in staggered rows, as shown in FIG. 11, in two roughly parallel rows that permits increasing the number of pull plates created on the surface of the same test piece while leaving each plate the space necessary for the pull means that act on the plate and the test piece during the test.

Mold elements 27a, 27b can be made separately, for example, according to the process corresponding to that illustrated in FIG. 10.

Mold elements 27a, 27b can also be made by cutting a mold 2 made in a single piece in a first step.

In a second method for implementing the third step of the process, pull plate or plates 6 are released after hardening of hardenable material 5 by destroying mold 2, thus designed by nature for a single use, for example, by mechanical means such as cutting and removal of pieces of the mold.

To implement this method, mold 2 is preferably made of a material that is less costly and easy to remove mechanically without the risk of damaging pull plates 6 or test piece 1.

As shown in FIGS. 14a and 14b, such a mold 2 is created, for example, by means of an expandable foam 76, for example a polyurethane foam, that can fill the space between two discs 74, 75, each having a part 72, 73 in the shape of pull plate 6 whose hollow cavity 3 is desired. After expansion and hardening of foam 76, discs 74, 75 are removed, leaving the cavity for at least one pull plate in foam 76 that is used as mold 2 in order to apply the process according to the invention.

After the pull plates are hardened, it is possible to remove foam 76 of the mold by cutting and scraping without damaging the pull plates.

The shapes of hardened hardenable material 5 corresponding to the volume of the pouring shafts, vents, and other connection channels that are not part of pull plates 6 are eliminated, for exampling, by removing them by means of tweezers.

In order to create pull plates 6 adapted to the tests, it is essential that the hardenable material 5 that is used has adhesion and mechanical strength characteristics after hardening that are compatible with the pulling forces applied during the test.

A suitable hardenable material 5 should be selected according to the type of coating applied onto test piece 1. Such materials are to be found, preferably, among glues and polymerizable or fusible resins such as polymers of the epoxy family.

During the tests conducted to select suitable materials, epoxy resin polymers, acrylic resins and polyurethane resin, and, in particular, structural epoxy glues permitted creating pull plates 6 whose adhesion to the tested surface and mechanical strength permit conducting the majority of tests on paints and varnishes used in the industry.

In order to improve the strength of a pull plate 6 so as to conduct tests with greater tearing forces, or to create a pull plate 6 with a hardenable material 5 of weaker mechanical strength once hardened, a core 65 of mechanical strength that is greater than that of hardened hardenable material 5, for example a metal core, is inserted, approximately in the axis of pull plate 6, during pouring, or after pouring, but before the hardening of hardenable material 5, as illustrated in FIG. 4 or FIG. 5.

Such a core 65, of a single use, is made, for example, of a bar of material chosen for the insert, in a section compatible with the section of plate 6 and of the desired length, i.e., close to the height of the pull plate.

Since it does not require quality machining, nor strict dimensional tolerance, nor a particular surface state, the cost of such a core is minimal.

Advantageously, as illustrated in FIG. 4, core 65 comprises a shoulder 68 positioned on said core to be located in plate 6 at the level of the zone used by the pulling means to pull on the plate and thus limit the risk of breaking the upper part of the plate.

In one particular implementation of the process, core 65 is held in the hollow form 3 of the mold in the desired positioned by means of mold 2. For example, as illustrated in FIG. 5, hollow form 3 of mold 2 has a recess 42 at its upper face 34 that can hold core 65 during the pouring operation.

Advantageously, the shape of pull plate 6 is adapted to facilitate the implementation of the process during the second and third steps of the process.

Thus, without the adaptations of the shape of pull plate 6 changing the desired contact surface of pull plate 6 with test piece 1, and without these adaptations causing the possibility of exerting the pulling force of the test on the plate, the angular forms of pull plate 6 can be softened, for example, by means of coupling neck-molding pieces 66a, 66b in FIG. 15a and/or inclined surfaces 67a, 67b, 67c in FIG. 15b. In particular, these modifications of form are chosen so that the risk of imprisoning air pockets during the second step of the process during filling of hollow form 3 with hardenable material 5 is minimized and so that the operation of removal from the mold during the third step of the process is facilitated.

The invention claimed is:

1. A method of constructing multiple pull plates on a coating for testing the adherence of the coating to a substrate comprising:
    applying the coating to a surface of the substrate to form a test piece;
    constructing a mold assembly having multiple mold cavities for forming multiple pulling elements, said pulling elements shaped to allow a pulling force to be applied thereto;
    applying the mold assembly to the test piece at an interface, wherein at least one wall of the multiple mold cavities is formed by the test piece;
    filling the multiple cavities with a liquid material to form the multiple pulling elements, wherein said liquid material is a polymerizable material;
    bonding the pulling elements to the test piece by polymerizing the liquid material in the multiple cavities; and
    removing the mold from the test piece to provide access to the pulling elements; and
    perform a series of adherence tests on the test piece by applying forces to each of the pulling elements to determine the adherence of the coating to the substrate.

2. The process according to claim 1 in which the interface between the multiple mold cavities and the wall formed by the test piece is kept tightly sealed.

3. The process according to claim 2 wherein the interface is kept tightly sealed, by constructing a portion of the mold assembly at the interface to conform to the dimensions and contours of the test piece and wherein the test piece is constructed according to a test protocol being implemented; and further by constructing the mold assembly of a material that can deform according to the contour of the test piece.

4. The process according to claim 2 wherein the interface is kept tightly sealed, by means of a bead of material on the multiple mold cavities forming an excrescence at the interface.

5. The process according to claim 2 wherein the interface is kept tightly sealed, by means of a removable joint positioned in a recess constructed around the interface.

6. The process according to claim 1 in which the multiple mold cavities are filled with the liquid material through openings in the multiple mold cavities located other than at the interface.

7. The process according to claim 6 in which said openings correspond roughly to an upper surface of the pull plates.

8. The process according to claim 6 in which said openings correspond to one end of pouring shafts emerging into the multiple mold cavities.

9. The process according to claim 6 in which said openings corresponds to one end of an injection channel leading into the multiple mold cavities.

10. The process according to claim 1 in which air contained in the multiple mold cavities is evacuated during the filling of said multiple mold cavities with liquid material.

11. The process according to claim 1 wherein the mold assembly is constructed of a deformable material and the mold assembly is removed from the test piece by utilizing the capacity of the mold assembly to be deformed.

12. The process according to claim 1 in which the mold assembly is constructed in at least two separable elements, and the mold assembly is removed from the test piece by separating the two separable elements.

13. The process according to claim 1 wherein the mold assembly is destroyed to remove the mold from the test piece.

14. The process according to claim 1 wherein the mold assembly is constructed of a silicone resin.

15. The process according to 1 wherein the shapes of the multiple mold cavities have coupling neck-molding pieces constructed to minimize the risk of imprisoning air pockets while pouring the liquid material and to facilitate the removal of the mold assembly from the test piece.

16. The process according to claim 15 wherein the coupling neck-molding pieces are formed with inclined surfaces.

17. The process according to claim 1 wherein the liquid material is chosen from the group comprising epoxy resins, acrylic resins and polyurethane resins.

18. The process according to claim 1 wherein a core of greater strength than the polymerized liquid material is inserted in approximate alignment with a longitudinal axis of the multiple mold cavities before or during the pouring operation of the liquid material.

19. The process according to claim 18 wherein the core is made with a shoulder positioned while pouring liquid material, in a zone of the multiple mold cavities to provide a means by which the force may be applied to the pulling element.

20. The process according to claim 1 wherein the pulling elements are formed having a longitudinal axis and the longitudinal axis of the pulling element is positioned perpendicular to the test piece when the molds are applied to the test piece.

21. The process according to claim 1 further comprising constructing at least one injection opening, communicating with distribution passages connecting the multiple mold cavities, to allow the distribution of the liquid material to the multiple cavities.

22. The process according to claim 21 wherein the multiple mold cavities are arranged in a star shaped pattern in the mold assembly, and each of said multiple mold cavities is constructed with at least one vent.

23. The process according to claim 21 further comprising at least one vent opening situated so that, while pouring liquid material through said injection opening, said multiple mold cavities are filled progressively by the liquid material and air contained in the multiple mold cavities is evacuated by the at least one vent without being opposed.

* * * * *

UNITED STATES PATENT AND TRADEMARK OFFICE
CERTIFICATE OF CORRECTION

| | |
|---|---|
| PATENT NO. | : 8,096,190 B2 |
| APPLICATION NO. | : 11/673003 |
| DATED | : January 17, 2012 |
| INVENTOR(S) | : Stephane Rey |

It is certified that error appears in the above-identified patent and that said Letters Patent is hereby corrected as shown below:

First Page, Column 1, Line 1, (75) Inventor, before "Lacasse" insert -- Lavernose --.

Signed and Sealed this
Tenth Day of April, 2012

David J. Kappos
*Director of the United States Patent and Trademark Office*